United States Patent [19]

Marsoner et al.

[11] Patent Number: 4,501,296

[45] Date of Patent: Feb. 26, 1985

[54] DEVICE FOR CHARGING AN ELECTROCHEMICAL MEASURING APPARATUS

[75] Inventors: Hermann Marsoner; Karl Harnoncourt; Helmut List, all of Graz, Austria

[73] Assignee: AVL AG, Schaffhausen, Switzerland

[21] Appl. No.: 547,589

[22] Filed: Nov. 1, 1983

[30] Foreign Application Priority Data

Nov. 19, 1982 [AT] Austria ................................ 4229/82

[51] Int. Cl.³ ............................................ F16K 11/02
[52] U.S. Cl. .......................... 137/625.41; 137/624.13; 204/409; 251/249.5
[58] Field of Search .............................. 204/275, 409; 137/625.41, 624.13, 896, 602, 891; 251/249.5

[56] References Cited

U.S. PATENT DOCUMENTS

| 2,477,975 | 8/1949 | Frock | 251/249.5 |
|---|---|---|---|
| 2,482,167 | 9/1949 | Gilmont | 137/625.41 |
| 3,069,025 | 12/1962 | Winkler et al. | 137/624.13 |
| 3,503,412 | 3/1970 | Schuler | 137/625.41 |
| 3,536,451 | 10/1970 | Ludwin | 137/624.13 X |
| 3,556,950 | 1/1971 | Dahms | 204/409 X |
| 3,586,049 | 6/1971 | Adamson | 137/625.41 |
| 3,840,048 | 10/1974 | Moen | 137/625.41 |
| 3,916,950 | 11/1975 | Morgerson et al. | 137/625.41 |
| 3,980,093 | 9/1976 | Rhine et al. | 137/624.13 X |
| 4,115,235 | 9/1978 | Capone | 204/409 X |

FOREIGN PATENT DOCUMENTS 748123 12/1966 Canada ............................... 204/409

Primary Examiner—G. L. Kaplan
Assistant Examiner—Nam X. Nguyen
Attorney, Agent, or Firm—Watson, Cole, Grindle & Watson

[57] ABSTRACT

An electrochemical measuring apparatus may be charged with an option of several media by providing a feeder part with the respective media connections, and by guiding a piece of pipe in a bore, which is sealed off and is movable relative to this feeder part. On its end facing away from a measuring chamber in the apparatus, the piece of pipe has a connection for additional media. Besides, it carries at least one circumferential bore which may be brought to coincide with at least one of the input openings into the bore connecting to the feed lines, by means of a relative motion - preferably controlled via a stepping motor - between the pipe piece and the above bore.

3 Claims, 2 Drawing Figures

DEVICE FOR CHARGING AN ELECTROCHEMICAL MEASURING APPARATUS

BACKGROUND OF THE INVENTION

The present invention relates to a device for charging an electrochemical measuring apparatus alternatively with test-, reference- or cleaning media, the device comprising a control unit carrying input fittings for the various media and connecting them with a feed line into a measuring chamber of the apparatus.

DESCRIPTION OF THE PRIOR ART

Chemical analyses employing such measuring facilities, e.g., blood gas analyses, determine a combination of measurement values, using measuring chambers with sensors of a known kind. Among the values measured are, for example, the pH-value of a blood sample, the partial pressure of oxygen in molecular solution, and the partial pressure of $CO_2$. A measuring apparatus utilizing electrochemical sensors for measurement of the three above mentioned parameters, is described, for instance, in Austrian Patent No. 349.151. This type of measuring apparatus is usually mounted in a metal supporting frame controlled by a thermostat. This frame will keep the measuring chamber itself at a constant temperature—for blood gas analyses usually at 37° Centigrade—and will provide for a tight seal of the sensitive tips of the measuring sensors for the above three parameters, in the area of contact with the chamber containing the sample medium.

The measuring chamber must contain a device permitting it to be charged with sample materials of various kinds or with reference liquids and/or gases.

For this purpose a known device of this type makes use of a rotatable element configured as a circular disk containing a number of openings placed along a circle, which may be connected to the feeder line of the measuring chamber by means of an automatically controlled or manually effected rotation. On the side of the rotatable element facing away from the measuring chamber, connecting tubes may be attached for containers of chemicals or gases. In addition, the measuring chamber may be connected via this known element with a vessel for cleaning solution and with a waste container into which the used sample may be sucked by evacuation. The same process will also cause the cleaning solution to be sucked into the chamber. At the end of the cleaning process the rotatable element is positioned such that outside air may be sucked in for drying out the chamber.

With this known device the sample itself may also be fed into the measuring chamber via a certain position of the rotatable element. For this purpose a capillary tube containing the sample is inserted at a suitable configured site of the element. In the above mentioned position of the rotatable element the output opening of the measuring chamber is connected to a peristaltic pump which will slowly suck the sample into the measuring chamber. The output of the peristaltic pump goes into a waste container.

This known type of device has a number of disadvantages; the rotatable element must seal tightly against the measuring chamber in all its connecting positions. The rotating motion will exert certain stresses upon the sealing elements which are made from some elastic material, thereby causing abrasion. The abraded particles may block the narrow connecting bores from and to the measuring chamber. This abrasion will eventually cause leakages in the connection between rotatable element and measuring chamber, leading to operational failures.

The sample is taken in via the rotatable element, leaving behind a solied area in this element which is not cleaned after sample intake. In the case of blood measurements, for instance, this will give rise to an unhygienic zone which may be blocked by coagulated blood.

SUMMARY OF THE INVENTION

It is an object of the present invention to avoid the above mentioned disadvantages of the known type of charging device for the measuring apparatus. According to the invention this is achieved by providing the control unit with a feeder part carrying the input fittings, and with a piece of pipe positioned in a bore of the feeder part against which it is sealed such that it may be moved relative to the feeder part, and by making the fittings open into the bore, and by providing the piece of pipe with at least one bore in its circumference such that by means of a relative motion between pipe and bore, the circumferential bore may cooperate with at least one of the input openings into the bore, the input fitting for the sample and for the cleaning medium being directly connected to the end of the pipe piece facing away from the measuring chamber.

This kind of sample feed will ensure that no residues will remain in the charging device after the sample has been entered into the measuring chamber, thus guaranteeing reliable functioning. Configuration of the control unit of the charging device according to the invention will also eliminate the disadvantages of the known variant with regard to sealing the charging device, the extremely small sealing surface in the area of the circumferential bore of the pipe required by the new variant being of particular advantage.

In a further embodiment of the present invention the piece of pipe is held in the bore in such a way that it may be rotated around its axis, and that its end facing the measuring chamber is rotatably sealed against the feed line into the chamber, while the end away from the measuring chamber is rotatably sealed against the input fitting of the sample feed; in addition, a positioning element driven via a stepping motor is mounted on the piece of pipe to effect a controlled rotation. Although it would also be possible in principle to control the medium feed by means of a relative axial shift between feeder part and pipe, the rotational movement described above will allow a simpler design of the device, the stepping motor—which may be controlled most precisely—permitting fast and precise switching between the individual medium feed lines to be connected to the measuring chamber.

In this context it is of particular advantage if the input openings of the individual fittings into the bore of the feeder part are located each in at least one plane normal to the axis of the bore, since in this case only one sealed circumferential bore for each such plane will have to be provided on the piece of pipe.

Although a suitable choice of material and tolerances would enable the piece of pipe itself to be sealed sufficiently tight directly against the bore in the feeder part, a more preferable design is proposed in another embodiment of the invention, according to which an additional seal is provided in the area of the circumferential bore of the pipe, which will provide a seal against the input openings in the feeder part.

DESCRIPTION OF THE DRAWING

The following is a more detailed description of an embodiment of the invention as illustrated by the enclosed drawing, in which.

DESCRIPTION OF A PREFERRED EMBODIMENT

Figure 1:
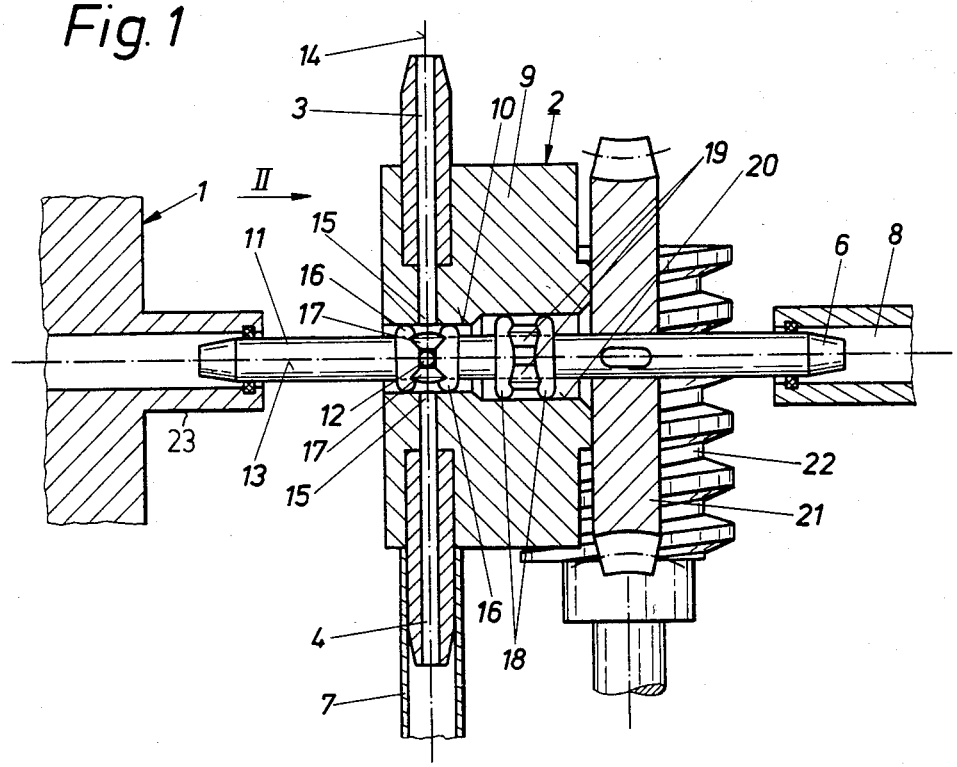
FIG. 1 shows a section through a charging device for an electrochemical measuring apparatus according to the present invention.
Figure 2:
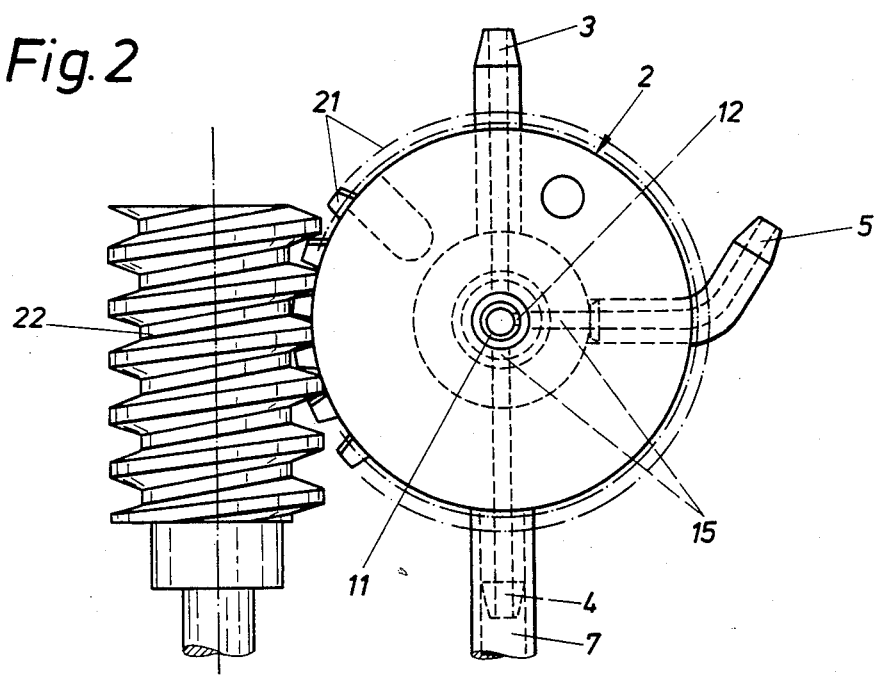
FIG. 2 presents a view along arrow II in FIG. 1.

A device for charging an electrochemical measuring apparatus 1 alternatively with sample-, reference- or cleaning media, parts of which are indicated only schematically, has a control unit 2, with connections or input fittings 3, 4, 5, 6 for the individual media, the diagram showing respective tubes and pipes 7, 8 of fittings 4 and 6 only. The control unit 2 has a feeder part 9 and a piece of pipe 11 held in a bore 10 of the feeder part 9 against which it is sealed such that it may be rotated relative to the feeder part 9. The wall of pipe piece 11 has radically extending bore 12.

Fittings 3, 4, 5, which may be supplied with reference media or buffering agents (not shown here) required for adjusting or operating the electrochemical apparatus whose mode of operation is irrelevant for the purpose of the present invention, are presented here with their axes on a plane 14 normal to axis 13 of bore 10, the input openings 15 of the individual media fittings or connections coinciding with the circumferential bore 12 one after the other, when the pipe piece 11 is rotated around axis 13. The radial bore 12 is provided with separate sealing lips 16, 17 made, for instance, of vulcanised-on rubber bead. Similar rubber beads 18, 19 are provided on pipe piece 11 in an enlarged section 20 of bore 10 at a distance from the circumferential bore 12 on the right hand side; they are only used for guiding the piece of pipe 11 against the bore, however.

Connection 6 which is positioned on the end of pipe piece 11 facing away from the measuring apparatus, is directly used for feeding in the sample, and, at the end of the sample feeding process, for feeding a cleaning or drying medium, which will ensure that the sample path within the charging device may be cleaned in an easy and reliable way, and that no deposits will develop, which would interfere with the operation of the charging device.

The relative rotation between control unit 2 and pipe piece 11, which is needed for the alternative opening of one of the input openings 15 via the radial bore 12, is effected by a worm wheel 21 attached to the pipe piece 11 and rotating together with it, which may be rotated by a stepping motor (not shown here) via a worm 22. For this purpose the ends of pipe piece 11 are sealed rotatably in the feed line 23 for the measuring chamber (not shown) of the measuring apparatus 1, and also in the tube 8 for the feed of sample or cleaning medium.

The device shown here will permit, for instance, the supply of a reference medium via one of the connections 3, 4, 5 at the beginning of a measurement with the use of measuring apparatus 1, pipe piece 11 having been rotated for this purpose by means of a worm wheel 21 such that the respective input opening 15 is working together with the circumferential bore 12; in this case, the tube 8 will have been closed by a closing element (not shown here), such as a squeeze valve. Turning the pipe piece 11 by 90 degrees will then cause one of the other connections in plane 14 to cooperate with the radial bore 12, thus enabling another reference medium or a buffer solution to be fed in. A subsequent rotation of the pipe piece 11 will cause the radial bore 12 to assume a position in which there is no cooperation with any of input openings 15, e.g., in the place opposite of the opening of connection 5, permitting sample medium to flow in from there, for example, as soon as the above closing element in tube 8 has opened. At the end of the measurement, and after the sample feed path has been cleaned, the process as described above may start anew, this time, for instance, initiating a measurement of other sample constituents.

We claim:

1. A device for charging an electrochemical measuring apparatus alternatively with sample, reference and cleaning media, comprising a fixed feed line for a measuring chamber of said apparatus, a control unit having separate input fittings respectively for the media and for connecting said fittings to said feed line, said control unit comprising a feeder part having a through bore, said input fittings for only the reference media being carried by said feeder part and having openings communicating with said bore, a fixed conduit for the sample and cleaning media, a pipe section extending through said bore and being rotatable about its central axis relative to said bore and relative to said feed line and said conduit, means for sealing said pipe section against the wall of said bore, the wall of said pipe section having at least one radial bore capable of communicating with said reference media openings one at-a-time upon relative rotation between said pipe section and said feeder part bore, one end of said pipe section extending into said feed line and being rotatably sealed thereagainst, an opposite end of said pipe section facing away from the measuring chamber defining one of said input fittings for the sample and cleaning media, said one input fitting extending into said conduit and being rotatably sealed thereagainst, and means cooperating with said pipe section to effect controlled rotation thereof.

2. A device according to claim 1, wherein said input fittings for the reference media lie in a plane normal to said central axis.

3. A device according to claim 1, wherein additional means is provided for sealing said openings relative to said feeder part bore.

* * * * *